United States Patent
Cameretti et al.

(10) Patent No.: US 11,370,752 B2
(45) Date of Patent: Jun. 28, 2022

(54) PROCESS FOR PREPARING CYCLODODECANONE

(71) Applicant: Evonik Operations GmbH, Essen (DE)

(72) Inventors: Luca Cameretti, Dortmund (DE); Jan Caßens, Datteln (DE); Ralf Meier, Dortmund (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/482,981

(22) PCT Filed: Jan. 31, 2018

(86) PCT No.: PCT/EP2018/052356
§ 371 (c)(1),
(2) Date: Aug. 1, 2019

(87) PCT Pub. No.: WO2018/141771
PCT Pub. Date: Aug. 9, 2018

(65) Prior Publication Data
US 2019/0345101 A1    Nov. 14, 2019

(30) Foreign Application Priority Data

Feb. 3, 2017  (DE) .................... 102017000989.9

(51) Int. Cl.
| | | |
|---|---|---|
| *C07D 201/04* | (2006.01) | |
| *C07C 45/48* | (2006.01) | |
| *C07C 49/413* | (2006.01) | |
| *C07C 49/307* | (2006.01) | |
| *C07D 201/10* | (2006.01) | |

(52) U.S. Cl.
CPC .......... *C07D 201/10* (2013.01); *C07C 49/307* (2013.01)

(58) Field of Classification Search
CPC ..... C07D 201/04; C07C 45/48; C07C 49/413; C07C 49/307

USPC .......................................... 568/338; 540/464
See application file for complete search history.

(56) References Cited

U.S. PATENT DOCUMENTS

| | | | |
|---|---|---|---|
| 7,449,606 B2 | 11/2008 | Teles et al. | |
| 7,838,705 B2 | 11/2010 | Teles et al. | |
| 9,000,223 B2 | 4/2015 | Micoine et al. | |
| 9,533,932 B2 * | 1/2017 | Micoine | C07C 45/512 |
| 9,533,933 B2 * | 1/2017 | Micoine | C07C 45/002 |

FOREIGN PATENT DOCUMENTS

| | | |
|---|---|---|
| EP | 2223911 A1 | 9/2010 |
| EP | 2772478 A1 | 9/2014 |
| GB | 1101611 A | 1/1968 |
| JP | H05977 A | 1/1993 |
| WO | 2005030689 A2 | 4/2005 |
| WO | 2005030690 A2 | 4/2005 |

OTHER PUBLICATIONS

Balbolov, E. Kh., et al., New Routes to Cyclododecanone, XP002157471, Asen Zlatarov University, Burgas, Bulgaria, Russian Journal of General Chemistry, vol. 67, No. 6, 1997 (6 pages).

PCT International Search Report dated Jun. 8, 2018 corresponding to PCT Application No. PCT/EP2018/052356 filed Jan. 31, 2018 (17 pages).

Thomas Schiffer, et al. Cyclododecanol, Cyclododecanone, and Laurolactam; 2005 Wiley-VCH Verlag GmbH & Co. KGaA, Weinheim; 10.1002/1435607.a08_201 (5 pages).

* cited by examiner

*Primary Examiner* — Bruck Kifle
(74) *Attorney, Agent, or Firm* — Linda S. Li; Jason S. Ngui; Andrew H. Chung

(57) ABSTRACT

The invention relates to a method for producing cyclododecanone (CDON). During the production, contaminated cyclododecane (CDAN) is produced. This can be separated from CDON by distillation (CDAN-containing fraction). The separation of CDAN and impurities such as 13-oxabicyclo [7.3.1]tridecane occurs by crystallizing out CDAN from the CDAN-containing fraction.

9 Claims, No Drawings

PROCESS FOR PREPARING CYCLODODECANONE

This Application is a 35 U.S.C. § 371 U.S. national stage of PCT International Application No. PCT/EP2018/052356, filed Jan. 31, 2018, which claims the benefit of German Application No. 102017000989.9, filed Feb. 3, 2017, the contents of each of which are hereby incorporated by reference in their entirety into this application.

The present invention relates to a process for producing cyclododecanone, a process for purifying cyclododecane and a process for producing laurolactam.

Cyclododecanone (CDON) is obtained by the known processes of Bashkirow oxidation of cyclododecane (CDAN; Oenbrink, G. and Schiffer, T. 2009. Cyclododecanol, Cyclododecanone, and Laurolactam. Ullmann's Encyclopedia of Industrial Chemistry). Alternatively, EP-A-2772478 (U.S. Pat. No. 9,000,223) describes the epoxidation of cyclododecene (CDEN) to afford cyclododecane epoxide (CDAN epoxide) and subsequent rearrangement thereof to afford CDON. Both the recited processes form not only the main product CDON but also cyclododecanol (CDOL) and saturated and unsaturated linear and cyclic C11-alkanes. Also formed are further oxidized species, inter alia linear 2-undecanone and the cyclic ring ethers 13-oxabicyclo[8.2.1]tridecane (1,4-C12-ether) and/or 13-oxabicyclo[7.3.1]tridecane (1,5-C12-ether) in a concentration of up to 1 wt % respectively, based on the resulting CDON-containing mixture. Specifically these three last-mentioned components cannot be distillatively removed from CDAN at reasonable economic outlay due to the unexpected boiling behaviour thereof and are accordingly passed back to the oxidation after the multi-stage distillative fractionation of the product mixture together with the CDAN unconverted in the oxidation and/or formed in the rearrangement of CDAN epoxide to afford CDON. Here, the secondary components are in part oxidized further, as a result of which they become more water-soluble and, acting as compatibilizers, can have a negative effect on phase separation and further contaminate the process wastewater. However, in part they continue to be recirculated and accumulate in the process until they find an outlet in the target product CDON and negatively affect the purity thereof.

An obvious alternative to distillation for the removal of 2-undecanone and 1,4-C12-ether and 1,5-C12-ether is the introduction of an additional reaction stage in which the recited components are converted into species that are lower or higher boiling compared to CDAN in order to be able to subsequently distil these off more easily. Especially for the linear ketone, available reactive processes include the hydrogenation of the keto group to afford an alcohol over suitable fixed bed catalysts containing for example palladium, ruthenium, copper or nickel or aldol condensation over acid catalysts. High conversions of >90% could be achieved for 2-undecanone by hydrogenation. In the hydrogenation of the C12-ethers under harsh conditions (20 bar hydrogen, 200° C.) the 1,5-C12-ether proved particularly resistant and stable while the 1,4-C12-ether was converted to components higher boiling than CDAN with up to 90% conversion. Under the reaction conditions CDAN was in part even converted to cyclic C11-products which was not desired.

In laboratory experiments high conversions of >90% were only achieved for CDAN/2-undecanone mixtures with para-toluenesulfonic acid as catalyst for aldol condensation. However, para-toluenesulfonic acid is not suitable for converting C12-ether. In further experiments CDAN/2-undecanone/C12-ether mixtures were reacted over strongly acidic catalysts containing aluminium oxide, silicon oxide, titanium oxide or mixtures thereof. Here too, the 1,5-C12-ether proved to have low reactivity—conversions of no more than 10% were achieved. For 2-undecanone as well, conversions of no more than merely 50% were achieved. Economic removal was achieved for the 1,4-C12-ether alone.

The options provided in the prior art constitute additional, complex process steps. Furthermore, the 1,5-C12 ether cannot be removed in any process and the 2-undecanone can be removed only in one process.

The present invention accordingly has for its object the provision of a process for producing CDON which makes it possible to simultaneously remove impurities being formed. Ideally, CDAN present after the reaction to afford CDON should be isolated. Simultaneously, impurities having a similar vapor pressure to CDAN, in particular 2-undecanone, 1,4-C12-ether and also 1,5-C12-ether, should be removed from CDAN.

It has been found that, surprisingly, the CDAN produced in the described production processes which cannot be purified by distillation or combinations of reaction with distillation may be derived in high purity by crystallization.

There has accordingly been found a process of the type described at the outset for producing cyclododecanone (CDON) which comprises the steps of:
a) reaction of 1,5,9-cyclododecatriene (CDT) to afford a mixture of cyclododecanol (CDOL) and CDON,
b) dehydrogenation of the CDOL to afford CDON, wherein a CDON-containing mixture which comprises cyclododecane (CDAN) is obtained,
c) distillation of the CDON-containing mixture to obtain a fraction comprising CDAN (CDAN-containing fraction) and a CDON-containing fraction, and
d) crystallizing-out CDAN from the CDAN-containing fraction.

The CDAN-containing fraction may contain impurities such as 13-oxabicyclo[8.2.1]tridecane, 13-oxabicyclo[7.3.1]tridecane, 2-undecanone or mixtures thereof. It is important to remove in particular these impurities having vapor pressures similar to CDAN, since a distillation is not suitable. In contrast with the prior art these may be removed simultaneously with the CDON process according to the invention (i.e. in a single process step). Particularly preferably, 13-oxabicyclo[7.3.1]tridecane can be removed with the process since the prior art does not describe a process for the removal of CDAN.

The mixture of CDOL and CDON may be obtained by the consecutive steps of i) hydrogenation of CDT to afford CDAN and ii) oxidation of CDAN to afford the mixture of CDOL and CDON.

The mixture may alternatively be obtained by the consecutive steps of i) hydrogenation of CDT to afford cyclododecene (CDEN), II) epoxidation of CDEN to afford cyclododecane epoxide (CDAN epoxide) and III) rearrangement of CDAN epoxide to afford the mixture of CDOL and CDON.

The crystallized-out CDAN from step d) may be reused. It may be oxidized to afford a mixture of CDOL and CDON for example. It is alternatively possible to convert the CDAN into cyclododecanone oxime with nitrosyl chloride.

The CDON-containing mixture obtained after dehydrogenation of CDOL to afford CDON (step b) is subsequently distilled (step c). This affords a fraction which comprises not only CDAN but also further compounds which compared to CDAN have an approximately identical or higher vapour pressure (CDAN-containing fraction). The abovementioned impurities are contained in this fraction. A fraction which has a lower vapor pressure compared to CDAN remains; this fraction contains inter alia the CDON (CDON-containing fraction).

For further processing of the CDON it is advantageous to isolate the CDON from the CDON-containing fractions. To this end it is preferable to remove the CDON by distillation.

The CDAN-containing mixture in step d) is typically sent to a crystallization unit and crystallized-out. Suitable methods are melt crystallization or solution crystallization. In melt crystallization the CDAN contained for example in the impurified CDAN stream partly solidifies on a cooled surface, wherein the secondary components can be concentrated in the so-called mother liquor which remains liquid and can be separated from the CDAN crystals. Subsequently, impurities incorporated in the CDAN crystals are sweated-out and removed by raising the temperature before finally CDAN is obtained in very high purity by melting. High yields can be achieved by a multi-stage process. The melt crystallization is preferably selected from static crystallization, falling film crystallization or suspension crystallization. In a particularly preferred embodiment of the invention the CDAN-containing mixture is initially subjected to a crystallization and the uncrystallised constituents are removed. This is followed by a temperature increase for dissolution (sweating) of impurities. Crystallized-out CDAN in high concentration remains.

Before CDAN is crystallized-out from the CDAN-containing fraction it is preferable to perform a distillation. This allows removal of further substances such as low boilers which could disrupt crystallization. Low boilers are compounds which have a higher vapor pressure compared to CDAN.

The present invention further relates to a process for purifying CDAN originating for example from the production process for cyclododecanone according to the Bashkirow process or the epoxidation process. The CDAN contains impurities such as for example 13-oxabicyclo[8.2.1]tridecane, 13-oxabicyclo[7.3.1]tridecane, 2-undecanone or mixtures thereof. The purification is effected by means of crystallization, for example melt crystallization or solution crystallization.

The stream originating from the oxidation or the rearrangement comprises the mixture of CDOL and CDON. Also present are about 0-2 wt % of low boilers (lower boiling than CDAN), 5-15 wt % of CDAN or CDEN, 0-1 wt % of middle boilers (boiling point between CDAN and CDON), 70-80 wt % of CDON, CDOL and high boilers (higher boiling than CDOL). The stream is sent to a first distillation column in which the separation step between middle boilers and CDON is selected. Pure CDON and a CDOL-rich fraction are derived from the bottoms product.

The invention further provides a process for producing laurolactam. This comprises initially producing CDON from CDT (CDON process according to the invention). The CDON is subsequently oximated to afford cyclododecanone oxime (CDON oxime). Suitable reaction partners are hydrogen peroxide and ammonia which form hydroxylamine in situ. This is followed by rearrangement of CDON oxime, for example using cyanuric chloride or sulfuric acid, to afford laurolactam.

EXAMPLES

In the following examples CDAN fractions removed from a CDON-containing mixture by distillation were employed.

The CDON-containing mixture was obtained by epoxidation of CDEN and subsequent rearrangement. THE CDAN fraction was worked up in different ways in the examples.

The impurities were determined by gas chromatography-mass spectrometry (GC-MS). GC instrument Agilent GC 6890/Agilent MSD 5973; separating column 60 m×0.25 mm DB-Wax, film 0.25 μm; injector: 250° C., split 50:1, 244 kPa Helium; oven temperature 150° C.-5° C./min-180° C. (10 min)-5° C./min-220° C. (40 min); injection 1 μL sample; ionisation: electron impact ionization, 70 eV, and chemical ionization using ammonia as reactant gas.

Example A: Acid Catalyst (Noninventive)

A mixture according to table 1 was boiled over several hours at 230° C. over an acidic aluminosilicate powder. Final conversions of about 27% for the 2-undecanone and about 45% for the 1,5-C12-ether in each case based on the employed feed were obtained. The 1,4-C12-ether was decomposed to below the limit of detection.

TABLE 1

Conversion according to example A

| wt % | CDAN | 2-undecanone | 1,5-C12-ether | 1,4-C12-ether | remainder |
| --- | --- | --- | --- | --- | --- |
| feed | 91.86% | 3.73% | 0.05% | 0.23% | 4.13% |
| after 20 h | 91.77% | 2.74% | 0.03% | | 5.47% |

Example B: Hydrogenation (Noninventive)

A mixture consisting of CDAN and both C12-ethers was hydrogenated for 21 h at 200° C. under an H2 atmosphere (20 bar) over a Ru catalyst. The CDAN was partly cracked into cyclic C11 components. The 1,4-C12-ether was converted to an extent of 90%, but the 1,5-C12-ether only to an extent of 10%, in each case based on the employed feed.

TABLE 2 conversion according to example B

| wt % | C11 | CDAN | 1,5-C12-ether | 1,4-C12-ether | remainder |
| --- | --- | --- | --- | --- | --- |
| feed | | 98.90% | 0.56% | 0.50% | 0.04% |
| after 21 h | 13.97% | 85.48% | 0.43% | 0.05% | 0.07% |

Example C: Hydrogenation (Noninventive)

A mixture consisting of CDAN and 2-undecanone was hydrogenated for 68 h at 200° C. under an H2 atmosphere (20 bar) over a Ru catalyst. The 2-undecanone was converted to an extent of 97% based on the employed feed.

TABLE 3 hydrogenation according to example C

| wt % | C11 | CDAN | 2-undecanone | remainder |
| --- | --- | --- | --- | --- |
| feed | | 95.89% | 4.03% | 0.08% |
| 68 h | 1.07% | 95.41% | 0.12% | 3.40% |

Example 1 (Inventive)

1439 g of an industrial CDAN-containing fraction containing not only CDAN but also cyclic and non-cyclic C11-hydrocarbons, oxidized C11- and C12-constituents such as 1,4-C12-ether, 1,5-C12-ether and 2-undecanone according to table 4 was melted at 70° C. in a glass container. Upon reaching a temperature at which the complete mixture was in the form of a melt, the temperature was reduced via a separately temperature-controllable cooling finger submerged in the middle of the container. This was effected such that the surface temperature of the cooling finger was reduced at a constant cooling gradient of 0.5 K/minute until an appreciable amount of solid had formed at the cooling finger surface. At the end of the experiment the remaining mother liquor from the crystallization was separated from the crystals adhering to the cooling finger by discharging the mother liquor and then analysed. Subsequently, by slowly increasing the cooling finger temperature, a sweat fraction of 1.44 g was melted off, withdrawn and analyzed by gas chromatography. Subsequently the crystals were melted off the cooling finger, withdrawn separately and analyzed by gas chromatography. Table 4 summarizes the amount and the gas chromatography analytical results for the various fractions.

TABLE 4

Purification of a CDAN-containing fraction

| fraction | | feed | mother liquor | sweat fraction | crystal fraction |
|---|---|---|---|---|---|
| fraction amount | g | 1439.0 | 1206.6 | 11.4 | 221.0 |
| CDAN | area % | 97.5 | 97.2 | 97.4 | 99.0 |
| C11-components | area % | 1.6 | 1.8 | 1.7 | 0.6 |
| 2-undecanone | area %-% | 0.3 | 0.3 | 0.3 | 0.1 |
| 1,4-C12-ether | area % | 0.1 | 0.1 | 0.1 | 0.0 |
| 1,5-C12-ether | area % | 0.1 | 0.1 | 0.1 | 0.0 |
| remainder | area % | 0.4 | 0.4 | 0.4 | 0.3 |

The crystallizing-out according to the invention increased the purity of CDAN from 97.5% to 99.0%. The proportion of byproducts in the CDAN was reduced from 2.5% to 1.0%; in particular the difficult-to-separate substances 2-undecanone and the two C12-ethers were reduced/no longer detectable.

Example 2 (Inventive)

182 g of the crystal fraction from example 1 were melted in a smaller experimental apparatus and subsequently subjected to static crystallization. Via the separately temperature-controllable cooling finger submerged in the middle the surface of the cooling finger was in turn cooled at a temperature gradient of 0.5 K/minute and a crystal layer generated at the surface of the cooling finger.

At the end of the experiment the remaining mother liquor from the crystallization was separated from the crystals by discharging the mother liquor and then analysed. Subsequently, by slowly increasing the cooling finger temperature a sweat fraction of 0.8 g was melted off, withdrawn and analyzed by gas chromatography. Subsequently the crystals were melted off the cooling finger, withdrawn separately and analyzed by gas chromatography. Table 5 summarizes the amount and the gas chromatography analytical results for the various fractions.

TABLE 5

Purification of the crystal fraction from example 1

| fraction | | feed | mother liquor | sweat fraction | crystal fraction |
|---|---|---|---|---|---|
| fraction amount | g | 182 | 142.98 | 0.8 | 38.22 |
| CDAN | area % | 99.0 | 98.8 | 99.3 | 99.6 |
| C11-components | area % | 0.6 | 0.7 | 0.4 | 0.2 |
| 2-undecanone | area % | 0.1 | 0.1 | 0.0 | 0.0 |
| remainder | area % | 0.3 | 0.3 | 0.3 | 0.2 |

Static crystallizing-out of CDAN having an initial purity of 99.0% increased the purity of CDAN to 99.6%. The proportion of byproducts in the CDAN was reduced by more than half. 2-Undecanone was no longer detectable.

Example 3 (Inventive)

1367 g of an industrial CDAN-containing fraction containing not only CDAN but also an elevated concentration of cyclic and non-cyclic C11-hydrocarbons, oxidized C11- and C12-constituents such as 1,4-C12-ether, 1,5-C12-ether and 2-undecanone according to table 6 was melted at 70° C. in a glass container. Upon reaching a temperature at which the complete mixture was in the form of a melt, the temperature was reduced via a separately temperature-controllable cooling finger submerged in the middle of the container. This was effected such that the surface temperature of the cooling finger was reduced at a constant cooling gradient of 0.5 K/minute until an appreciable amount of solid had formed at the cooling finger surface. At the end of the experiment the remaining mother liquor from the crystallization was separated by discharging the mother liquor and then analysed. Subsequently, by slowly increasing the temperature a sweat fraction of 12.4 g was melted off, withdrawn and analyzed by gas chromatography. Subsequently the crystals were melted off the cooling finger, withdrawn separately and analyzed by gas chromatography. Table 6 summarizes the amount and the gas chromatography analytical results for the various fractions.

TABLE 6

Purification of a CDAN-containing fraction

| fraction | | feed | mother liquor | sweat fraction | crystal fraction |
|---|---|---|---|---|---|
| fraction amount | g | 1367.0 | 1164.2 | 5.3 | 197.5 |
| CDAN | area % | 93.1 | 92.3 | 97.5 | 97.6 |
| C11-components | area % | 5.8 | 6.4 | 2.2 | 2.2 |
| 2-undecanone | area % | 0.5 | 0.6 | 0.1 | 0.0 |
| 1,4-C12-ether | area % | 0.1 | 0.1 | 0.0 | 0.0 |
| 1,5-C12-ether | area % | 0.2 | 0.2 | 0.0 | 0.0 |
| remainder | area % | 0.3 | 0.3 | 0.2 | 0.2 |

The crystallizing-out according to the invention increased the purity of CDAN from 93.1% to 97.6%. The proportion of byproducts in the CDAN was reduced from 6.9% to 2.4%. 2-Undecanone and the C12-ethers were no longer detectable after crystallization.

The invention claimed is:
1. A process for the purification of cyclododecane (CDAN) comprising the consecutive steps of:
   a) reaction of 1,5,9-cyclododecatriene (CDT) to afford a mixture of cyclododecanol (CDOL) and CDON,
   b) dehydrogenation of the CDOL to afford CDON, wherein a CDON-containing mixture which comprises cyclododecane (CDAN) is obtained,
   c) distillation of the CDON-containing mixture to obtain a fraction comprising CDAN (CDAN-containing fraction) and a CDON-containing fraction, and d) crystallizing-out CDAN from the CDAN-containing fraction by melt crystallization or solution crystallization; and wherein the mixture of CDOL and CDON is obtained by the consecutive steps of
i) hydrogenation of CDT to afford CDAN and
ii) oxidation of CDAN to afford the mixture of CDOL and CDON; or wherein the mixture of CDOL and CDON is obtained by the consecutive steps of
I) hydrogenation of CDT to afford cyclododecene (CDEN),
II) epoxidation of CDEN to afford cyclododecane epoxide (CDAN epoxide) and
III) rearrangement of CDAN epoxide to afford the mixture of CDOL and CDON.

2. The process according to claim 1, wherein the CDAN-containing fraction contains impurities which comprise 13-oxabicyclo[8.2.1]tridecane, 13-oxabicyclo[7.3.1]tridecane, 2-undecanone or mixtures thereof.

3. The process according to claim 2, wherein the impurity comprises 13-oxabicyclo[7.3.1]tridecane.

4. The process according to claim 1, wherein the crystallized-out CDAN (step d) is oxidized to afford a mixture of CDOL and CDON.

5. The process according to claim 1, wherein the crystallized-out CDAN (step d) is converted into cyclododecanone oxime with nitrosyl chloride.

6. The process according to claim 1, wherein the CDON is removed from the CDON-containing fraction by distillation.

7. The process according to claim 1, wherein the CDAN-containing fraction is distilled to remove low boilers before the crystallizing-out.

8. The process according to claim 1, wherein the melt crystallization is selected from static crystallization, falling film crystallization or suspension crystallization.

9. The process for purifying cyclododecane (CDAN),
wherein the CDAN contains impurities selected from 13-oxabicyclo[8.2.1]tridecane, 13-oxabicyclo[7.3.1]tridecane, 2-undecanone or mixtures thereof,
wherein the CDAN is crystallized-out by crystallization selected from melt crystallization or solution crystallization.

* * * * *